US012728062B2

(12) United States Patent
Zheng et al.

(10) Patent No.: US 12,728,062 B2
(45) Date of Patent: Sep. 8, 2026

(54) METHOD AND DEVICE FOR CONVERTING CURRENT AND MOMENT AND REHABILITATION ROBOT

(71) Applicant: Zhengzhou Angelexo Intelligent Technologies Co., Ltd., Zhengzhou (CN)

(72) Inventors: Pengyuan Zheng, Zhengzhou (CN); Liguo Li, Zhengzhou (CN); Jianhui Wang, Zhengzhou (CN); Jianwei Chen, Zhengzhou (CN); Yanjun Fan, Zhengzhou (CN); Luya Li, Zhengzhou (CN); Sen Yang, Zhengzhou (CN)

(73) Assignee: ZHENGZHOU ANGELEXO INTELLIGENT TECHNOLOGIES CO., LTD., Zhengzhou (CN)

( * ) Notice: Subject to any disclaimer, the term of this patent is extended or adjusted under 35 U.S.C. 154(b) by 0 days.

(21) Appl. No.: 18/019,756

(22) PCT Filed: Oct. 24, 2022

(86) PCT No.: PCT/CN2022/127035
§ 371 (c)(1),
(2) Date: Feb. 3, 2023

(87) PCT Pub. No.: WO2023/245937
PCT Pub. Date: Dec. 28, 2023

(65) Prior Publication Data

US 2025/0120870 A1 Apr. 17, 2025

(30) Foreign Application Priority Data

Jun. 21, 2022 (CN) ........................ 202210706465.3

(51) Int. Cl.
*A61H 1/02* (2006.01)
*B25J 9/16* (2006.01)
*G16H 40/63* (2018.01)

(52) U.S. Cl.
CPC .......... *A61H 1/0266* (2013.01); *B25J 9/1633* (2013.01); *G16H 40/63* (2018.01);
(Continued)

(58) Field of Classification Search
CPC .... A61H 2201/1659; A61H 2201/1207; A61H 1/02; A61H 2201/5007; A61H 2205/12;
(Continued)

(56) References Cited

U.S. PATENT DOCUMENTS 5,255,188 A * 10/1993 Telepko .................. A61H 1/02 601/40
10,537,283 B1 * 1/2020 Caputo .................... A61H 3/00
(Continued)

FOREIGN PATENT DOCUMENTS

CN 112179551 1/2021
CN 112405615 A * 2/2021 .......... B25J 19/0095

OTHER PUBLICATIONS

CN-112405615-A Spec Machine Translation (Year: 2025).*
(Continued)

*Primary Examiner* — Brandy S Lee
*Assistant Examiner* — Abigayle Dale
(74) *Attorney, Agent, or Firm* — FENWICK & WEST LLP

(57) ABSTRACT

Provided are a method and a device for converting a current and a moment and a rehabilitation robot, which relate to the technical field of current moment conversion. The method is applied to a controller of a rehabilitation robot; and the method comprises: acquiring to-be-processed current data; searching for a conversion relationship corresponding to the
(Continued)

to-be-processed current data from a pre-stored current conversion relationship table based on the to-be-processed current data, wherein the current conversion relationship table stores at least one set of corresponding relationships of current data and conversion relationship; and converting the to-be-processed current data into a corresponding target moment using the conversion relationships.

12 Claims, 4 Drawing Sheets

(52) U.S. Cl.
CPC ................ *A61H 2201/1207* (2013.01); *A61H 2201/1659* (2013.01); *A61H 2201/5007* (2013.01)

(58) Field of Classification Search
CPC .......... A61H 1/00; A61H 1/0237–0288; A61H 3/00; A61H 2205/106; G01L 5/0042; G16H 40/63; B25J 9/1638; B25J 9/1633; B25J 9/163; B25J 9/0006; G15H 40/63
See application file for complete search history.

(56) References Cited

U.S. PATENT DOCUMENTS

2015/0141878 A1* 5/2015 Roy ......................... A61H 1/02 601/34
2019/0336383 A1* 11/2019 Song ...................... A61H 1/024

OTHER PUBLICATIONS

CN 112405615 A Specification Machine Translation (Year: 2025).*
Chinese Patent Office, First Office Action, CN Application No. 202210706465.3, Apr. 11, 2024, 15 Pages.
Chinese Patent Office, Notification to Grant Patent Right for Invention of priority document, CN Application No. 202210706465.3, Mar. 6, 2025, 3 Pages.
Chinese Patent Office, Second Office Action, CN Application No. 202210706465.3, Nov. 3, 2024, 11 Pages.
International Patent Office, Search Report and Written Opinion, PCT Application No. PCT/CN2022/127035, Mar. 14, 2023, 15 pages.

* cited by examiner

METHOD AND DEVICE FOR CONVERTING CURRENT AND MOMENT AND REHABILITATION ROBOT

CROSS-REFERENCE TO RELATED APPLICATION

This application is a U.S. National Phase Application, filed under 35 U.S.C. § 371, of International Application No. PCT/CN2022/127035, filed Oct. 24, 2022, entitled "Method and Device for Converting Current and Moment and Rehabilitation Robot", which claims priority to Chinese patent application no. 202210706465.3, filed on Jun. 21, 2022, and entitled "Method and Device for Converting Current and Moment and Rehabilitation Robot". Each of foregoing disclosure is herein incorporated by reference herein in its entirety.

TECHNICAL FIELD

The present disclosure relates to the technical field of current moment conversion, and in particular, to a method and a device for converting a current and a moment and a rehabilitation robot.

BACKGROUND ART

Relevant rehabilitation robots mostly use a separate moment sensor to detect a torsional force during movement of a user. However, the moment sensor is expensive, and it is used together with a motor of the rehabilitation robot, causing that various operating power devices are associated with each other and affect each other by means of electromagnetic conduction, electromagnetic induction, and electromagnetic radiation. Under certain conditions, the operating devices may be interfered and affected, and in this case, the detection accuracy of the moment sensor is low.

In addition, weight and wearing comfort are crucial for a wearable rehabilitation robot, while the moment sensor and a mounting mechanical structure not only increase the total weight of the rehabilitation robot, but also are troublesome to wear, causing poor applicability of a relevant wearable rehabilitation robot.

SUMMARY

The present disclosure aims at providing a method and a device for converting a current and a moment and a rehabilitation robot, so as to solve the above problem of poor applicability of a relevant wearable rehabilitation robot.

An embodiment of the present disclosure provides a method for converting a current and a moment, wherein the method is applied to a controller of a rehabilitation robot; and the method may include: acquiring to-be-processed current data; searching for a conversion relationship corresponding to the to-be-processed current data from a pre-stored current conversion relationship table based on the to-be-processed current data, wherein the current conversion relationship table stores at least one set of corresponding relationships of current data and conversion relationship; and converting the to-be-processed current data into a corresponding target moment using the conversion relationships.

In an optional embodiment, an ankle joint motor of the above rehabilitation robot may be configured with load weights, and the method further may include: collecting a plurality of current data generated after placing the load weights on the ankle joint motor; calculating moment data corresponding to the current data generated by each of the load weights according to a pre-stored mass data of the load weights and a moment calculation formula; generating a current and moment curve based on the current data and the moment data corresponding to the current data; extracting a plurality of linear moment intervals in the current and moment curve; calculating a slope value of each linear moment interval, and saving the slope value as a conversion relationship corresponding to the linear moment interval; extracting a current value range of the linear moment interval on the current and moment curve; and associating and saving the current value range and the conversion relationship, so as to generate the current conversion relationship table.

In an optional embodiment, the above ankle joint motor of the rehabilitation robot may be configured with a cantilever, wherein the cantilever is coaxially disposed with a rotating shaft of the ankle joint motor; a scale mark is disposed on the cantilever, and the load weights are suspended at different scale mark positions of the cantilever.

In an optional embodiment, a plurality of current data corresponding to each moment data can form a current data set; the slope value can be determined through a following formula: $k=(y_{max}-y_{min})/(F_2-F_1)$, where $y_{max}$ is the maximum value of the current data in the current data set, $y_{min}$ is the minimum value of the current data in the current data set, $F_1$ is the minimum moment data value in the moment interval, and $F_2$ is the maximum moment data value in the moment interval.

In an optional embodiment, the above step of searching for a conversion relationship corresponding to the to-be-processed current data from a pre-stored current conversion relationship table may include: searching for a current value range to which the to-be-processed current data belongs from the pre-stored current conversion relationship table; and determining the conversion relationship corresponding to the found current value range as the conversion relationship corresponding to the to-be-processed current data.

In an optional embodiment, the above step of converting the to-be-processed current data into a corresponding target moment using the conversion relationships may include: generating a linear expression of conversion between the current and the moment according to the conversion relationship; and converting the to-be-processed current data into a corresponding target moment through the linear expression.

In an optional embodiment, the above step of collecting a plurality of current data generated after placing the load weights on the ankle joint motor may include: collecting a plurality of initial current data generated after placing the load weights on the ankle joint motor; and filtering the initial current data to obtain the current data.

In an optional embodiment, the above step of filtering the initial current data to obtain the current data may include: selecting a predetermined number of initial current data from a plurality of initial current data based on a preset sampling frequency; sorting the predetermined number of initial current data, and removing boundary data in the sorted predetermined number of initial current data to obtain residual current data; performing a linear regression on the residual current data; and determining an average value of the residual current data after the linear regression, and determining the average value as the current data.

In an optional embodiment, the above step of performing a linear regression on the residual current data may include: determining whether a difference value between every two adjacent residual current data in the residual current data is greater than a preset standard deviation; and if so, removing residual current data close to the boundary in two adjacent residual current data until the difference value between every two adjacent residual current data in the residual current data satisfies the preset standard deviation.

In an optional embodiment, the above residual current data are all sorted current data; and in the linear regression process, comparison is started from the minimum value to the maximum value in the sorted current data, or from the maximum value to the minimum value.

In an optional embodiment, the above rehabilitation robot correspondingly has a force arm length and an ankle joint motion angle, as well as a sitting and lying adjustment angle corresponding to a foot pedal of the rehabilitation robot; the step of calculating moment data corresponding to the current data generated by each load weight according to pre-stored mass data of the load weights and a moment calculation formula includes: acquiring the force arm length and the ankle joint motion angle of the rehabilitation robot, as well as the sitting and lying adjustment angle corresponding to the foot pedal of the rehabilitation robot, so as to obtain influencing parameter values corresponding to the moment calculation formula; and substituting the influencing parameter values and the mass data of the load weights into the moment calculation formula for calculation, so as to obtain moment data corresponding to the current data generated by each load weight, wherein the moment calculation formula is: $M=F*L*\cos|(\alpha-\delta)|$.

In an optional embodiment, the above sitting and lying adjustment angle is read by an encoder at a sitting and lying adjustment joint of the rehabilitation robot, and the ankle joint motion angle is read by the ankle joint encoder of the rehabilitation robot, wherein when a user uses the rehabilitation robot and lifts up a foot, an angle of the ankle joint motion angle is a positive value, and when the user uses the rehabilitation robot and puts down the foot, the angle of the ankle joint motion angle is a negative value.

An embodiment of the present disclosure further provides a device for converting a current and a moment, wherein the device may be applied to a controller of a rehabilitation robot; and the device may include: a data acquisition module, configured to acquire to-be-processed current data; a conversion relationship determination module, configured to search for a conversion relationship corresponding to the to-be-processed current data from a pre-stored current conversion relationship table based on the to-be-processed current data, wherein the current conversion relationship table stores at least one set of corresponding relationships of current data and conversion relationship; and a data conversion module, configured to convert the to-be-processed current data into a corresponding target moment using the conversion relationships.

An embodiment of the present disclosure further provides a rehabilitation robot, wherein the rehabilitation robot may be configured with the above device for converting a current and a moment.

An embodiment of the present disclosure further provides electronic equipment, wherein the electronic equipment includes a memory, a processor, and a computer program stored on the memory and executable on the processor, wherein the processor, when executes the computer program, implements the steps of the above method.

An embodiment of the present disclosure further provides a computer-readable storage medium, wherein the computer-readable storage medium stores a computer program, and wherein the computer program, when executed by the processor, implements the steps of the above method.

The embodiments of the present disclosure brings about the following beneficial effects:

the embodiments of the present disclosure provide the method and the device for converting a current and a moment and the rehabilitation robot, and relate to the technical field of current moment conversion. The method is applied to the controller of the rehabilitation robot. The method includes: acquiring to-be-processed current data; searching for a conversion relationship corresponding to the to-be-processed current data from a pre-stored current conversion relationship table based on the to-be-processed current data, wherein the current conversion relationship table stores at least one set of corresponding relationships of current data and conversion relationship; and converting the to-be-processed current data into a corresponding target moment using the conversion relationships. The method and the device for converting a current and a moment and the rehabilitation robot provided in the embodiments of the present disclosure can directly obtain the target moment by referring to the to-be-processed current data and the above current convention relationship table, without additionally installing a moment measurement structure to the rehabilitation robot, thus reducing the weight and decreasing the costs.

In addition, when the motor is at any specific moment value, the current of the motor fluctuates continuously, and it is difficult to obtain a current value corresponding to a specific moment value or a moment value corresponding to a specific current value by a conventional method, resulting in a low control precision. Moreover, even for the same motor, the moment and the current are not in a single stable linear relationship in different intervals of the moment. The current conversion relationship table provided in the embodiments of the present disclosure stores at least one set of corresponding relationships of current data and conversion relationship, and when the current data obtained is different, the target moment obtained is in a different moment interval, and further the corresponding moment is controlled to directly point to the corresponding moment interval, ensuring the control precision.

In the embodiments of the present disclosure, the moment detection is realized through the current of the rehabilitation robot itself. Compared with the case that the moment sensor and the motor are used together and affect each other, the moment detection of the present disclosure has a high accuracy and good stability.

Other features and advantages of the embodiments of the present disclosure will be illustrated in subsequent description, or some features and advantages may be deduced from the description or undoubtedly determined, or obtained by implementing the above technology of the present disclosure.

In order to make the above objectives, features, and advantages of the embodiments of the present disclosure more apparent and understandable, preferred embodiments are particularly illustrated below in combination with attached accompanying drawings to make following detailed description.

BRIEF DESCRIPTION OF DRAWINGS

In order to more clearly illustrate the technical solutions in specific embodiments of the present disclosure or in the prior art, drawings which need to be used in the description of the specific embodiments or the prior art will be introduced briefly below, and apparently, the drawings in the description below merely show some embodiments of the present disclosure, and a person ordinarily skilled in the art still could obtain other drawings in light of these drawings without creative efforts.

DETAILED DESCRIPTION OF EMBODIMENTS

Technical solutions of the present disclosure will be described clearly and completely below in combination with embodiments, and apparently, the embodiments described are only some, but not all embodiments of the present disclosure. Based on the embodiments in the present disclosure, all of other embodiments, obtained by a person ordinarily skilled in the art without using creative efforts, shall fall within the scope of protection of the present disclosure.

Relevant rehabilitation robots mostly use a separate moment sensor to detect a torsional force during movement of a user. However, the moment sensor is expensive, and it is used together with a motor of the rehabilitation robot, causing that various operating power devices are associated with each other and affect each other in three manners of electromagnetic conduction, electromagnetic induction, and electromagnetic radiation. Under certain conditions, the running devices may be interfered and affected, and in this case, the detection accuracy of the moment sensor is low.

In addition, weight and wearing comfort are crucial for a wearable rehabilitation robot, while the moment sensor and a mounting mechanical structure increase the total weight and volume of the rehabilitation robot.

Based on the above problems, an embodiment of the present disclosure provides a method and a device for converting a current and a moment and an electronic equipment. This technology can be applied to a controller of the rehabilitation robot.

Figures 1, 2:
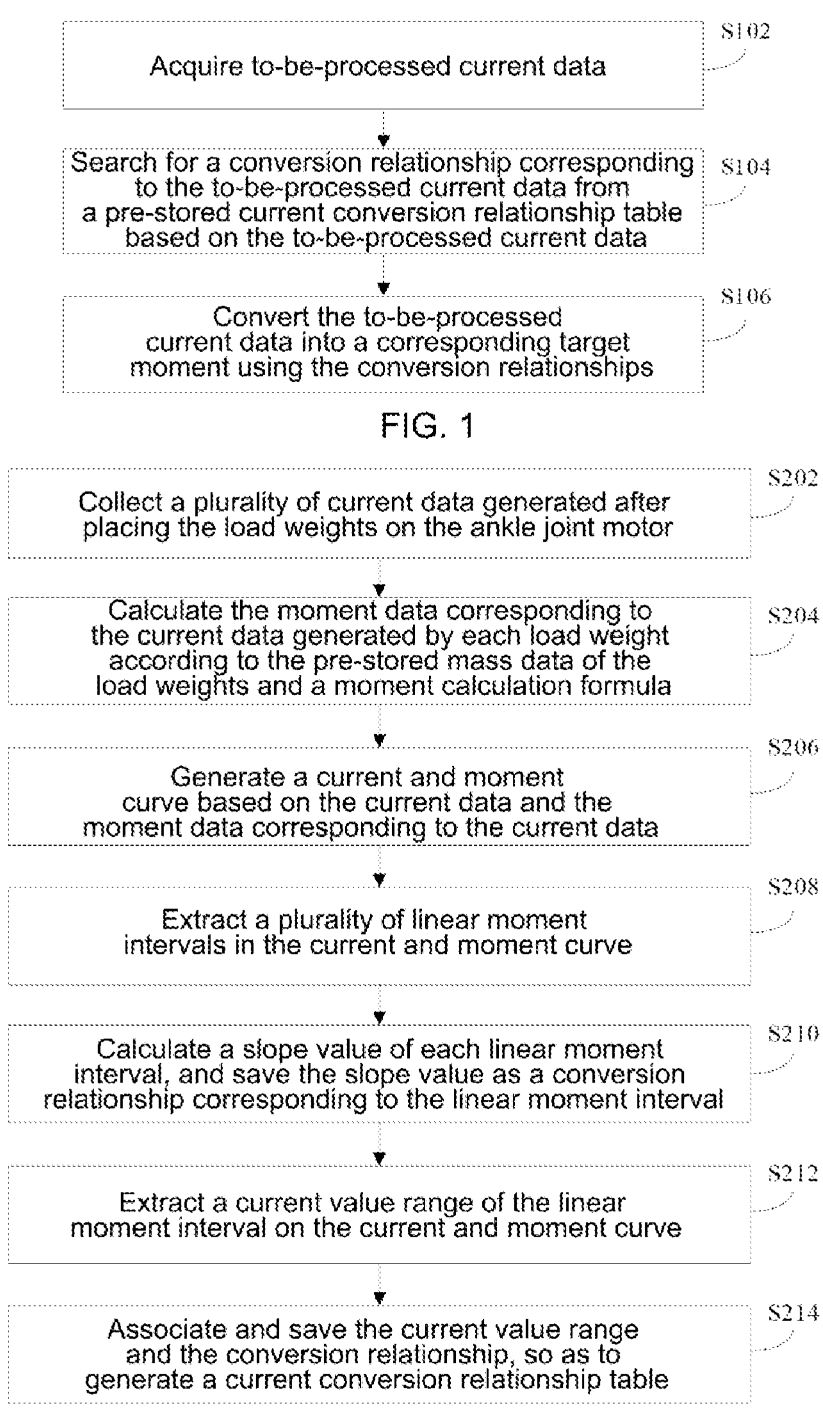
FIG. 1 is a flowchart of a method for converting a current and a moment provided in an embodiment of the present disclosure.
FIG. 2 is a flowchart of another method for converting a current and a moment provided in an embodiment of the present disclosure.

For ease of understanding of the present embodiment, a method for converting a current and a moment disclosed in an embodiment of the present disclosure is first described in detail. FIG. 1 shows a flowchart of the method for converting a current and a moment. As shown in FIG. 1, the method includes the following steps:

step S102, acquiring to-be-processed current data.

Specifically, after a user wears a rehabilitation robot and starts to use the same, an ankle joint motor of the rehabilitation robot starts to work. At this time, current data fed back during use can be obtained, and these current data can be all read by a program.

Step S104, searching for a conversion relationship corresponding to the to-be-processed current data from a pre-stored current conversion relationship table based on the to-be-processed current data.

Specifically, all the above to-be-processed current data have corresponding conversion relationships with a target moment, and these conversion relationships are stored in a pre-determined current conversion relationship table, so as to be capable of directly corresponding to a target moment numerical value of a given force according to the to-be-processed data.

Step S106, converting the to-be-processed current data into a corresponding target moment using the conversion relationships.

Specifically, the above conversion relationships are conversion conditions between the to-be-processed current data and moment data, therefore, according to the determined conversion relationships, a corresponding target moment can be directly obtained according to the to-be-processed current data without additionally installing a moment sensor, thus reducing the weight of the above rehabilitation robot and being capable of reducing costs.

In specific implementation, the current conversion relationship table stores at least one set of corresponding relationships of current data and the conversion relationship. When the numerical values of the above to-be-processed current data are different, the conversion relationships corresponding to the above to-be-processed current data are different, and different target moments can be obtained according to different conversion relationships.

An embodiment of the present disclosure provides a method for converting a current and a moment. This method can directly obtain the target moment by processing the to-be-processed current data and according to the pre-stored current conversion relationship table, without additionally installing a moment measurement structure to the rehabilitation robot, thus reducing the weight and decreasing the costs. In addition, the moment detection is realized by means of the currents of the rehabilitation robot itself. Compared with the case that the moment sensor and the motor are used together and affect each other, the moment detection in the present disclosure has a high accuracy and a good stability.

Optionally, in order to obtain the above current conversion relationship table in the embodiments of the present disclosure, an embodiment of the present disclosure further provides another method for converting a current and a moment. This method is implemented on the basis of the above method. In specific implementation, an ankle joint motor of the rehabilitation robot is configured with a cantilever and load weights, wherein the cantilever is coaxially disposed with a rotating shaft of the above ankle joint motor. Specifically, a scale mark is disposed on the above cantilever. The minimum unit of the scale mark length can be set according to the requirement, and in some embodiments, it may be set as 10 mm. The above load weights are suspended at different scale mark positions of the cantilever, so as to determine the moment required in the above current conversion relationship table according to the length corresponding to corresponding scale marks. Specifically, as shown in FIG. 2, a flowchart of another method for converting a current and a moment includes the following steps:

step S202, collecting a plurality of current data generated after the load weights are placed on the ankle joint motor.

In specific implementation, the above current data is determined through the following steps 10-11:

step 10, collecting a plurality of initial current data generated after the load weights are placed on the ankle joint motor.

Specifically, different current data corresponding to the ankle joint motor can be determined by using load weights with different masses. In specific implementation, after the above load weights with known mass are placed on the cantilever of the ankle joint motor, the above load weights will provide a force-bearing moment to the above ankle joint motor, and for the motor, the larger the force-bearing moment is, the load during the operation of the motor will be increased, and the larger the corresponding power loss is, the larger a feedback current will be generated by an inner closed loop. Therefore, the current data collected at this time is the current data corresponding to the above load weights with known mass.

Optionally, when the above ankle joint motor works, currents corresponding to the ankle joint motor are in a continuous fluctuating state, and all these currents are collected by a sensor, so as to obtain the above plurality of initial current data.

Optionally, the above plurality of initial current data further include a part of current data influenced by external factors, and these current data cannot accurately represent current data corresponding to the weight loads, and at this time, what needs to be collected is the current data which is not influenced by external factors.

In specific implementation, the above external factors may be current data according to the above load weights, which cannot accurately represent the current data corresponding to the load weights, therefore, the plurality of collected initial current data are current data when the force-bearing moment of the above ankle joint motor tends to be stable, so as to obtain current data which can show that it is only influenced by the above load weights.

Step 11, filtering the initial current data to obtain current data.

Specifically, the step of filtering the initial current data to obtain current data is determined through steps 20-23 below:

step 20, collecting a predetermined number of initial current data from a plurality of initial current data based on a preset sampling frequency.

In specific implementation, the above preset sampling frequency can be set by a user according to requirements, the above predetermined number may be a manually set number corresponding to current data that needs to be collected by a sensor. Optionally, the above predetermined number may be 50, that is, the sensor needs to collect 50 current data.

Specifically, the above sensor can collect the current of the above ankle joint motor according to the above preset sampling frequency, and stop collecting until the number collected meets the above predetermined number, so as to process the collected current data.

Step 21, sorting the predetermined number of initial current data, and removing boundary data in the sorted predetermined number of initial current data, so as to obtain residual current data.

Specifically, the above predetermined number of initial current data are discrete data, and has different sizes, therefore, these current data needs to be sorted first. Moreover, in order to obtain relatively accurate data in the above discrete data, boundary data in the sorted current data also needs to be filtered.

In specific implementation, the above initial current data may be sorted from small to large, and then 10 maximum current data and 10 minimum current data among 50 collected initial current data are screened out, and at this time, only 30 current data remain in the screened-out initial current data, and the 30 current data are the residual current data in the above.

Step 22, performing a linear regression on the residual current data.

Specifically, some relatively discrete current data may also exist in the above residual current data, and in this case, the residual current data also needs to be processed, so as to obtain further accurate current data, wherein in this case, the linear regression is performed on the above residual current data.

In specific implementation, the process of performing the linear regression on the residual current data is as follows:

(1) determining whether a difference value between every two adjacent residual current data in the residual current data is greater than a preset standard deviation; and (2) if so, removing residual current data close to the boundary in two adjacent residual current data until the difference value between every two adjacent residual current data in the residual current data satisfies the preset standard deviation.

Specifically, the above residual current data are all sorted current data, and in the linear regression process, comparison can be started from the minimum value to the maximum value in the above sorted current data, and can also be started from the maximum value to the minimum value. Then, it is judged whether a difference value between every two adjacent residual current data is greater than the preset standard deviation, wherein the above preset standard deviation may be determined according to user requirement, which is not limited herein.

In specific implementation, if numerical values corresponding to two adjacent residual current data are compared one by one from a minimum value to a maximum value, it is judged whether a difference between the two numerical values is large, wherein when the two data have a large difference therebetween, the residual current data corresponding to a relatively small numerical value is screened out. If numerical values corresponding to two adjacent residual current data are compared one by one starting from the maximum value to the minimum value, wherein when a difference between the two data is relatively large, the residual current data corresponding to the relatively large numerical value is screened out. The residual current data is stored until there is no significant difference between every two adjacent residual current data in the above residual current data.

Step 23, determining an average value of the residual current data after the linear regression, and determining the average value as the current data.

Specifically, after obtaining the above residual current data after the linear regression, the average value of these residual current data is also determined, and in this case, the average value is current data corresponding to the current load weights with known mass.

Step S204, calculating the moment data corresponding to the current data generated by each load weight according to the pre-stored mass data of the load weight and a moment calculation formula.

Specifically, the mass data of the load weights only represents a moment value of a contact point between the ankle joint motor of the rehabilitation robot and the machine, and in specific use, it is also necessary to dynamically balance moments of the user himself/herself and the rehabilitation robot, so as to obtain a "net moment" applied to the ankle joint by the rehabilitation robot. Specifically, in the process of movement of the ankle joint, the above "net moment" is also related to a force arm length of the rehabilitation robot, an ankle joint motion angle, and a sitting and lying adjustment angle corresponding to a foot pedal of the rehabilitation robot.

Therefore, in specific implementation, the ankle joint motion angle δ of the rehabilitation robot and the sitting and lying adjustment angle α corresponding to the foot pedal of the rehabilitation robot, and the force arm length corresponding to the rehabilitation robot need to be acquired, wherein the force arm length can be determined through conversion according to the length of the above load weights suspended on the above cantilever. These data are used to convert the mass data of the load weights into moment data in actual use, therefore, the above data is an influencing parameter value of the moment data, i.e., an influencing parameter value corresponding to the moment calculation formula.

The influencing parameter value and the mass data of the load weights are substituted into the moment calculation formula for calculation, so as to obtain actual moment data of the above current data corresponding to the rehabilitation robot.

Figure 7:
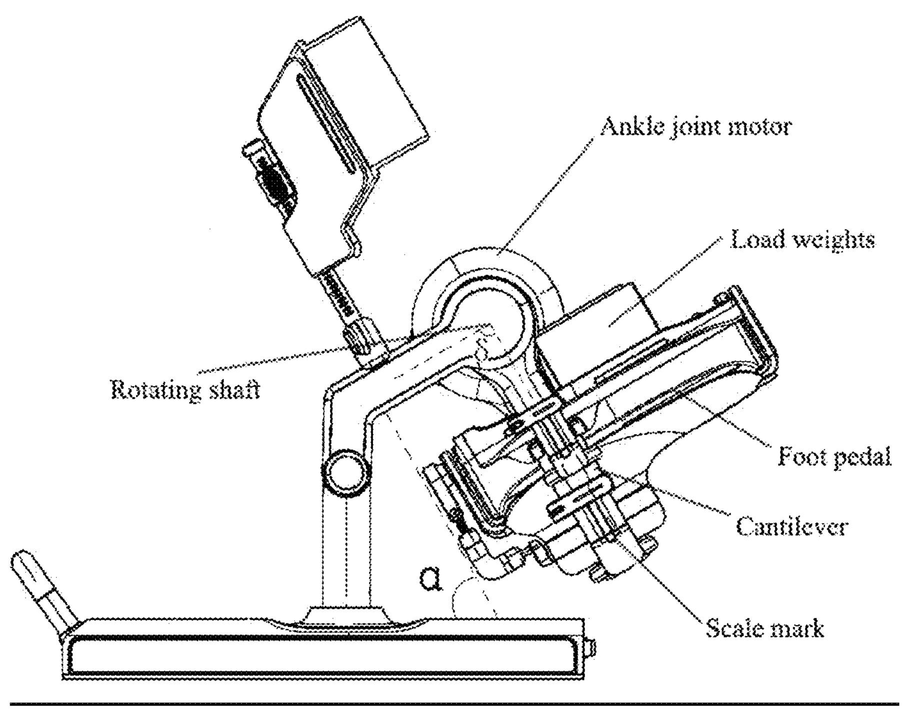
FIG. 7 shows a diagram of zero-position state of a rehabilitation robot provided in an embodiment of the present disclosure.

In the above, the moment calculation formula is: $M=F*L*\cos|(\alpha-\delta)|$, specifically, M is a balanced moment required for dynamic zero set during movement, i.e., moment data corresponding to the above current data. Optionally, for ease of understanding, the present embodiment shows a diagram of zero-position state of the rehabilitation robot as shown in FIG. 7. Specifically, in the above moment calculation formula, α is the sitting and lying adjustment angle, and δ is an ankle joint motion angle, wherein whether the sitting and lying adjustment angle α and the ankle joint motion angle δ are positive or negative is determined by a rotation situation when the angle δ is 90 degrees as shown in FIG. 7. When the rotation is upward, the angles are positive, and when the rotation is downward, the angles are negative. Optionally, the magnitude of numerical value of the above sitting and lying adjustment angle α and the magnitude of numerical value of the above ankle joint motion angle δ are both determined by the magnitude of the above rotation angle.

F is the weight added when the rehabilitation robot is used without exerting force. Specifically, when the above current conversion relationship table is determined, the numerical value corresponding to the above F may be a numerical value obtained by multiplying the mass corresponding to the above load weights by 0.98. L is the length indicated by the scale mark corresponding to the suspending position after the load weights are suspended on the cantilever of the ankle joint motor.

In specific implementation, the numerical value corresponding to the above M is a moment numerical value determined when $\alpha=0°$, $\delta=0°$, and the ankle height is determined.

Optionally, FIG. 7 shows the above sitting and lying adjustment angle α and ankle joint motion angle δ. Specifically, when the rehabilitation robot is turned on, the machine will automatically return to the zero-position state as shown in FIG. 7.

In the above, when the above rehabilitation robot is used, the above sitting and lying adjustment angle α can be read by an encoder at a sitting and lying adjustment joint of the rehabilitation robot, and a specific numerical value of the above sitting and lying adjustment angle α is obtained; and the above ankle joint motion angle δ can be read by the ankle joint encoder of the rehabilitation robot, and the specific numerical value of the above ankle joint motion angle δ is obtained, wherein when a user uses the rehabilitation robot and lifts up a foot, an angle of the above ankle joint motion angle δ is a positive value; and when the user uses the rehabilitation robot and puts down the foot, the angle of the above ankle joint motion angle δ is a negative value.

Step S206, generating a current and moment curve based on the current data and the moment data corresponding to the current data.

Specifically, the moment data corresponding to the above current data is an M value obtained by substituting the mass corresponding to the above load weights with known mass into the above moment calculation formula. Then, the M value is corresponding to the current data corresponding to the above load weights with known mass, and a one-to-one mapping relationship between the current data and the moment data can be obtained. Since the current data is obtained from continuously fluctuating discrete data after a data processing, the current data corresponding to different moment data has no stable single linear relationship.

Optionally, the current data corresponding to a plurality of load weights of different masses and the moment data corresponding to the load weights of each mass can be determined, in this case, a current and moment curve can be formed by a mapping relationship between each current data and each moment data.

In specific implementation, in the process of determining the above current and moment curve, the moment data corresponding to the above current data is actually moment data obtained by substituting the load weights with known mass into the above moment calculation formula when the above sitting and lying adjustment angle α is 0° and the ankle joint motion angle δ is 0°.

Step S208, extracting a plurality of linear moment intervals in the current and moment curve.

Step S210, calculating a slope value of each linear moment interval, and saving the slope value as a conversion relationship corresponding to the linear moment interval.

Specifically, when the motor is at any specific moment value, the current of the motor fluctuates continuously, and it is difficult to obtain a current value corresponding to a specific moment value or a moment value corresponding to a specific current value by a conventional method, resulting in low control precision. Moreover, even for the same motor, the moment and the current are not in a single stable linear relationship in different intervals of the moment. Thus, different functional relationships exist between the currents and the moments in different moment intervals.

In specific implementation, corresponding current data is obtained according to the above load weights with known mass, and according to the load weights and the influencing parameter values such as the force arm length L, the ankle joint motion angle δ, and the sitting and lying adjustment angle α of the above rehabilitation robot, the moment data corresponding to the load weights is obtained. After the current data and the moment data have the one-to-one mapping relationship, as the moment data is affected by the above influencing parameter values, the same moment data may be corresponding to a plurality of current data, and these current data have small fluctuations, and are distributed in a certain interval. Therefore, a plurality of linear moment intervals need to be extracted from the above current and moment curve, to determine a slope value between the current data and the moment data in each linear moment interval, so as to obtain different functional relationships between the currents and the moments in different moment intervals.

In specific implementation, the above linear moment interval may be a moment interval corresponding to a plurality of moment data selected by a user according to requirements. In the moment interval, a plurality of current data corresponding to each moment data exist in the moment interval. The plurality of current data corresponding to each moment data may form a current data set, and maximum value and minimum value of the current data exist in the current data set, wherein in this case, a ratio of a difference value between the maximum value and the minimum value of the current data to a moment value corresponding to the above moment interval is determined as the above slope value.

Specifically, the above slope value k can be determined through the following formula: $k=(y_{max}-y_{min})/(F_2-F_1)$, where $y_{max}$ is the maximum value of the current data in the above current data set, $y_{min}$ is the minimum value of the current data in the above current data set, $F_1$ is the minimum moment data value in the above moment interval, and $F_2$ is the maximum moment data value in the above moment interval.

In specific implementation, a coordinate system can be established according to the above current data and moment data, wherein the current data is used as a y-axis, and the moment data is used as an x-axis. After data measurement, a corresponding curve based on the current data and the moment data, and some discrete points on the curve can be obtained, wherein the discrete points comply with a linear rule as a whole. When the discrete points as a whole comply with the linear rule, a certain corresponding linear moment interval can be used as the above linear moment interval. Each linear moment interval can be measured and calculated, which corresponds to a conversion expression of corresponding current-moment: y=f(x).

Optionally, the above slope value can be used as a conversion relationship of the above conversion expression, that is, a function relationship of the conversion expression between the current data and the moment data.

Step S212, extracting a current value range of the linear moment interval on the current and moment curve.

Step S214, associating and saving the current value range and the conversion relationship, so as to generate a current conversion relationship table.

Specifically, as the above slope value is obtained based on the maximum value and the minimum value of the current data in the above current data set, a current value range is corresponding between the maximum value and the minimum value. Therefore, the slope value and the value range of the above current data further need to be associated and saved to obtain the current conversion relationship table, so that in the process of using the rehabilitation robot, the collected current data is directly corresponding to a preset moment interval according to the above current conversion relationship table, so as to obtain the required moment data.

An embodiment of the present disclosure provides another method for converting a current and a moment. In this method, load weights with known mass are suspended on an ankle joint motor, so as to obtain to-be-processed current data and moment data corresponding to the weight loads, wherein the current data and the moment data are in one-to-one correspondence, so as to obtain a corresponding target moment according to the current data. The moment determination method is quick and convenient.

Optionally, in an embodiment of the present disclosure, the to-be-processed current data obtained is further filtered, so as to solve the problem of low data accuracy brought about by data dispersion. Moreover, the above target moment is determined not only according to the load weights, but also according to the user and the influencing parameter values corresponding to the device of the rehabilitation robot. The above moment data can be balanced to the moment data in the process of using the rehabilitation robot, so that the conversion between moments and currents is more in line with the practical using process.

Figures 3, 4:
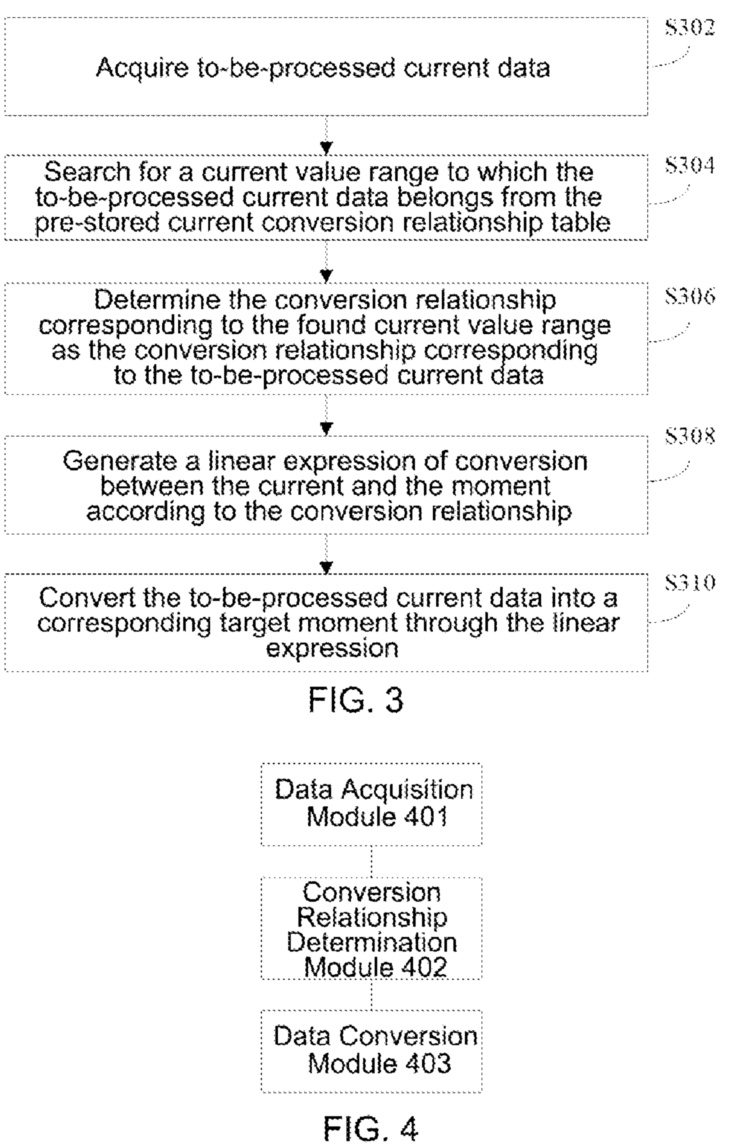
FIG. 3 is a flowchart of a further method for converting a current and a moment provided in an embodiment of the present disclosure.
FIG. 4 is a structural schematic view of a device for converting a current and a moment provided in an embodiment of the present disclosure.

Optionally, for ease of understanding, an embodiment of the present disclosure further provides another method for converting a current and a moment. This method is implemented on the basis of the above method. This method focuses on describing a process of searching for a conversion relationship corresponding to the to-be-processed current data from a pre-stored current conversion relationship table (implemented by the following steps S304-S306), and a process of converting the to-be-processed current data into a corresponding target moment using the conversion relationships (implemented by the following steps S308-S310). FIG. 3 shows a flowchart of a method for converting a current and a moment. The method includes the following specific steps:

step S302, acquiring to-be-processed current data.

Specifically, after a user wears the rehabilitation robot and starts to use the same, the ankle joint motor of the rehabilitation robot starts to work, wherein in this case, current data fed back during use can be obtained, and these current data are all collected by a sensor.

Step S304, searching for a current value range to which the to-be-processed current data belongs from the pre-stored current conversion relationship table.

After the current data is collected, the current value range to which these current data belong can be searched for from the above stored current conversion relationship table.

Step S306, determining the conversion relationship corresponding to the found current value range as the conversion relationship corresponding to the to-be-processed current data.

After the corresponding current value ranges are found according to the current data, these current value ranges may be corresponding to a corresponding conversion relationship, and this conversion relationship may also be expressed as a conversion relationship corresponding to the to-be-processed current data.

Step S308, generating a linear expression of conversion between the current and the moment according to the conversion relationship.

Specifically, as the conversion relationship is determined according to a corresponding linear moment interval, a corresponding linear moment interval can also be obtained after the conversion relationship is obtained, and a conversion expression y=f(x) corresponding to the linear moment interval is a linear expression for converting the current data and the moment data generated according to the conversion relationship.

Step S310, converting the to-be-processed current data into a corresponding target moment through the linear expression.

After a corresponding linear expression is obtained, the to-be-processed current data can be directly converted into a corresponding target moment.

Another method for converting a current and a moment provided in an embodiment of the present disclosure acquires, according to the to-be-processed current data obtained, a current value range to which the to-be-processed current data belongs, and obtains a corresponding conversion relationship according to the current value range, so as to obtain a corresponding linear expression according to the conversion relationship, and further obtain a moment corresponding to the to-be-processed current data. That is, in the embodiments of the present disclosure, different moments are determined according to current value ranges corresponding to different to-be-processed data, and even if the currents and the moments are not in a single linear relationship, an accurate moment interval can be directly determined, with high control precision.

Optionally, corresponding to the above method for converting a current and a moment as shown in FIG. 1, an embodiment of the present disclosure further provides a device for converting a current and a moment, the device being applied to a controller of a rehabilitation robot. FIG. 4 is a structural schematic diagram of a device for converting a current and a moment, including the following structures:

- a data acquisition module 401, configured to acquire to-be-processed current data;
- a conversion relationship determination module 402, configured to search for a conversion relationship corresponding to the to-be-processed current data from a pre-stored current conversion relationship table based on the to-be-processed current data, wherein the current conversion relationship table stores at least one set of corresponding relationships of current data and conversion relationship; and
- a data conversion module 403, configured to convert the to-be-processed current data into a corresponding target moment using the conversion relationships.

Optionally, the above conversion relationship determination module 402 is further configured to search for a current value range to which the to-be-processed current data belongs from the pre-stored current conversion relationship table; and determine the conversion relationship corresponding to the found current value range as the conversion relationship corresponding to the to-be-processed current data.

The above data conversion module 403 is further configured to generate a linear expression of conversion between the current and the moment according to the conversion relationship; and convert the to-be-processed current data into a corresponding target moment through the linear expression.

Figure 5:
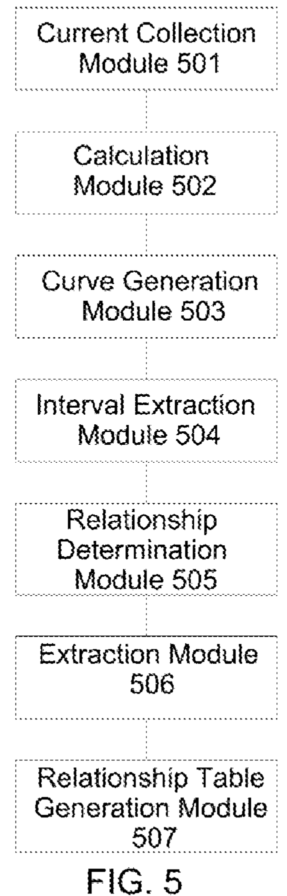
FIG. 5 is a structural schematic view of another device for converting a current and a moment provided in an embodiment of the present disclosure.

Optionally, corresponding to the flowchart of another method for converting a current and a moment shown in FIG. 2, an embodiment of the present disclosure further provides another device for converting a current and a moment. The structural schematic view of another device for converting a current and a moment as shown in FIG. 5 includes the following structures:

- a current collection module 501, configured to collect a plurality of current data generated after the load weights are placed on an ankle joint motor;
- a calculation module 502, configured to calculate moment data corresponding to the current data generated by each load weight according to the pre-stored mass data of the load weights and a moment calculation formula;
- a curve generation module 503, configured to generate a current and moment curve based on the current data and the moment data corresponding to the current data;
- an interval extraction module 504, configured to extract a plurality of linear moment intervals in the current and moment curve;
- a relationship determination module 505, configured to calculate a slope value of each linear moment interval, and save the slope value as a conversion relationship corresponding to the linear moment interval;
- an extraction module 506, configured to extract a current value range of the linear moment interval on the current and moment curve; and
- a relationship table generation module 507, configured to associate and save the current value range and the conversion relationship, so as to generate a current conversion relationship table.

Optionally, the above current collection module 501 is further configured to collect a plurality of initial current data generated after the load weights are placed on the ankle joint motor; and filter the initial current data to obtain current data.

The above current collection module 501 is further configured to select a predetermined number of initial current data from a plurality of initial current data based on a preset sampling frequency; sort the predetermined number of initial current data, and remove boundary data in the sorted predetermined number of initial current data, so as to obtain residual current data; perform linear regression on the residual current data; and determine an average value of the residual current data after the linear regression, and determine the average value as the current data.

The above current collection module 501 is further configured to determine whether a difference value between every two adjacent residual current data in the residual current data is greater than a preset standard deviation; and if so, remove residual current data close to the boundary in two adjacent residual current data until the difference value between every two adjacent residual current data in the residual current data satisfies the preset standard deviation.

The above calculation module 502 is further configured to acquire a force arm length and an ankle joint motion angle of the rehabilitation robot, as well as a sitting and lying adjustment angle corresponding to a foot pedal of the rehabilitation robot and a weight borne at the foot pedal, so as to obtain influencing parameter values corresponding to the moment calculation formula; and substitute the influencing parameter values and the mass data of the load weights into the moment calculation formula for calculation, so as to obtain moment data corresponding to the current data generated by each load weight, wherein the moment calculation formula is: $M=F*L*\cos|(\alpha-\delta)|$.

A person skilled in the art could clearly know that for the sake of convenience and conciseness of description, reference can be made to corresponding processes in the above method embodiments for specific operation processes of the device described in the above, which will not be repeated redundantly herein.

With regard to the embodiments of the above device for converting a current and a moment, an embodiment of the present disclosure further provides a rehabilitation robot, wherein the rehabilitation robot is configured with the above device for converting a current and a moment. For the description of the rehabilitation robot, reference can be made to the embodiments of the above device for converting a current and a moment, which will not be repeated redundantly herein.

An embodiment of the present disclosure further provides an electronic equipment, including a memory, a processor, and a computer program stored on the memory and executable on the processor, wherein when the processor executes the computer program, the steps of the method as shown in FIG. 1, FIG. 2, or FIG. 3 are implemented.

An embodiment of the present disclosure further provides a computer-readable storage medium, wherein the computer-readable storage medium stores a computer program; and when the computer program is executed by the processor, the steps of the method as shown in FIG. 1, FIG. 2, or FIG. 3 are implemented.

Figure 6:
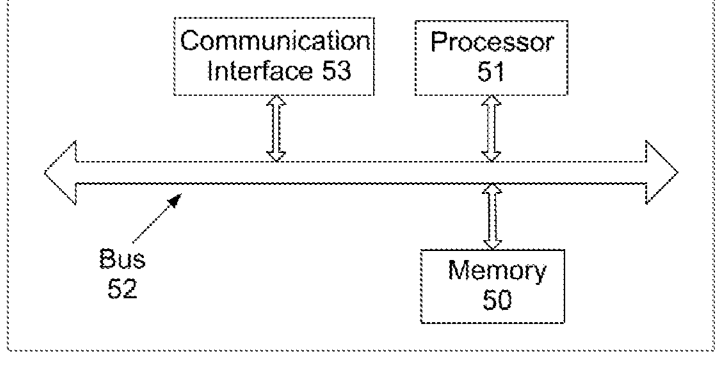
FIG. 6 is a structural schematic view of an electronic equipment provided in an embodiment of the present disclosure.

An embodiment of the present disclosure further provides a structural schematic view of electronic equipment, and as shown in FIG. 6, it is a structural schematic view of the electronic equipment. The electronic equipment includes a processor 51 and a memory 50, wherein the memory 50 stores computer-executable instructions that can be executed by the processor 51, and the processor 51 executes the computer-executable instructions so as to implement the method as shown in the above FIG. 1, FIG. 2, or FIG. 3.

In the embodiment shown in FIG. 6, the electronic equipment further includes a bus 52 and a communication interface 53, wherein the processor 51, the communication interface 53, and the memory 50 are connected via the bus 52.

In the above, the memory 50 may include high-speed random access memory (RAM), and also may include non-volatile memory, for example, at least one disk memory. Communication connection between this system network element and at least one other network element is achieved through at least one communication interface 53 (possibly wired or wireless), and Internet, Wide Area Network, local network, Metropolitan Area Network and so on may be used. The bus 52 can be an ISA (Industry Standard Architecture) bus, PCI (Peripheral Component Interconnect) bus or EISA (Extended Industry Standard Architecture) bus and so on. The bus 52 may include an address bus, a data bus, a control bus and so on. For ease of representation, the bus is represented merely with one two-way arrow in FIG. 6, but it does not mean that there is only one bus or one type of bus.

The processor 51 may be an integrated circuit chip, with a signal processing function. In an implementation process, various steps of the above method may be completed by an integrated logic circuit of hardware in the processor 51 or instruction in a software form. The above processor 51 may be a general-purpose processor, including Central Processing Unit (CPU for short), Network Processor (NP for short), etc., and also may be a Digital Signal Processor (DSP for short), an Application Specific integrated Circuit (ASIC for short), a Field-Programmable Gate Array (FPGA for short) or other programmable logic devices, discrete gates, transistor logic devices, or discrete hardware components. The general-purpose processor may be a microprocessor or the processor also may be any conventional processor and so on. The steps in the method disclosed in combination with the embodiments of the present disclosure may be directly carried out and completed by hardware decoding processor, or carried out and completed by a combination of hardware and software modules in the decoding processor. The software module may be located in a mature storage medium in the art such as a random access memory, a flash memory, a read-only memory, a programmable read-only memory or an electrically erasable programmable memory, and a register. The storage medium is located in the memory, and the processor 51 reads the information in the memory, and completes the method as shown in the preceding FIG. 1, FIG. 2, or FIG. 3 in combination with its hardware.

A computer program product of the method and the device for converting a current and a moment and the rehabilitation robot provided in embodiments of the present disclosure includes a computer readable storage medium in which a program code is stored, wherein instructions included in the program code can be used to execute the methods described in the method embodiments in the preceding. Reference can be made to the method embodiments for specific implementation, which will not be repeated redundantly herein.

The functions, if implemented in the form of software functional units and sold or used as an independent product, may be stored in a computer-readable storage medium. Based on such understanding, the technical solutions in essence or parts making contribution to the related art or parts of the technical solutions of the present disclosure may be embodied in form of a software product, and this computer software product is stored in a storage medium, including several instructions for making one computer device (which can be a personal computer, a server or a network device etc.) execute all or part of the steps of the methods of various embodiments of the present disclosure. The aforementioned storage medium includes various media in which program codes may be stored, such as U disk, mobile hard disk, Read-Only Memory (ROM), Random Access Memory (RAM), diskette and compact disk.

Finally, it should be explained that the various embodiments above are merely used for illustrating the technical solutions of the present disclosure, rather than limiting the present disclosure; although the detailed description is made to the present disclosure with reference to various preceding embodiments, those ordinarily skilled in the art should understand that they still could modify the technical solutions recited in various preceding embodiments, or make equivalent substitutions to some or all of the technical features therein; and these modifications or substitutions do not make the corresponding technical solutions essentially depart from the scope of the technical solutions of various embodiments of the present disclosure.

INDUSTRIAL APPLICABILITY

The embodiments of the present disclosure provide a method and a device for converting a current and a moment and the rehabilitation robot, and relates to the technical field of current moment conversion. The method is applied to the controller of the rehabilitation robot. The method includes: acquiring to-be-processed current data; searching for a conversion relationship corresponding to the to-be-processed current data from a pre-stored current conversion relationship table based on the to-be-processed current data, wherein the current conversion relationship table stores at least one set of corresponding relationships of current data and conversion relationship; and converting the to-be-processed current data into a corresponding target moment using the conversion relationships. The method and the device for converting a current and a moment and the rehabilitation robot provided in the embodiments of the present disclosure can directly obtain the target moment by referring to the to-be-processed current data and the above current convention relationship table, without additionally installing a moment measurement structure to the rehabilitation robot, thus reducing the weight and decreasing the costs.

In addition, when the motor is at any specific moment value, the current of the motor fluctuates continuously, and it is difficult to obtain a current value corresponding to a specific moment value or a moment value corresponding to a specific current value by a conventional method, resulting in low control precision. Moreover, even for the same motor, the moment and the current are not in a single stable linear relationship in different intervals of the moment. The current conversion relationship table provided in the embodiments of the present disclosure stores at least one set of corresponding relationships of current data and conversion relationship, and when the current data obtained is different, the target moment obtained is in a different moment interval, and further the corresponding moment is controlled to directly point to the corresponding moment interval, ensuring the control precision.

The method provided in the embodiments of the present disclosure realizes the moment detection by means of the current of the rehabilitation robot itself. Compared with the case that the moment sensor and the motor are used together and affect each other, the moment detection of the method provided in the embodiments of the present disclosure has a high accuracy and a good stability.

Besides, it may be understood that the method and the device for converting a current and a moment and the rehabilitation robot provided in the embodiments of the present disclosure may be reproduced, and may be used in a variety of industrial applications. For example, the method and the device for converting a current and a moment and the rehabilitation robot in the present disclosure can be used in the technical field of current moment conversion.

What is claimed is:

1. A method for converting a current and a moment, applied to a controller of a rehabilitation robot, wherein the controller is electrically connected to an ankle joint motor, an ankle joint encoder and a sitting and lying adjustment joint encoder of the rehabilitation robot; the ankle joint motor of the rehabilitation robot is configured with load weights and a cantilever, the cantilever is coaxially disposed with a rotating shaft of the ankle joint motor; scale marks are disposed on the cantilever, the load weights are suspended at corresponding scale mark positions of the cantilever, and the rehabilitation robot is correspondingly configured with a force arm length and an ankle joint motion angle, as well as a sitting and lying adjustment angle corresponding to a foot pedal of the rehabilitation robot, wherein the method comprises steps of:

acquiring a to-be-processed current data;

searching for a conversion relationship corresponding to the to-be-processed current data from a pre-stored current conversion relationship table based on the to-be-processed current data, wherein the current conversion relationship table stores at least one set of corresponding relationships between current data and the conversion relationship;

converting the to-be-processed current data into a corresponding target moment using the conversion relationship, collecting a plurality of current data generated after the load weights are placed on the ankle joint motor;

acquiring the force arm length and the ankle joint motion angle of the rehabilitation robot, as well as the sitting and lying adjustment angle corresponding to the foot pedal of the rehabilitation robot, so as to obtain influencing parameter values corresponding to the moment calculation formula;

substituting the influencing parameter values and the mass data of the load weights into the moment calculation formula for calculation, so as to obtain a moment data corresponding to the current data generated by each of the load weights, wherein the moment calculation formula is: $M=F*L*\cos|(\alpha-\delta)|$;

generating a current and moment curve based on the current data and the moment data corresponding to the current data;

extracting a plurality of linear moment intervals in the current and moment curve;

calculating a slope value of each of the linear moment intervals, and saving the slope value as a conversion relationship corresponding to the linear moment intervals;

extracting current value ranges of the linear moment intervals on the current and moment curve; and associating and saving the current value ranges and the conversion relationship, so as to generate the current conversion relationship table.

2. The method according to claim 1, wherein a plurality of current data corresponding to each moment data form a current data set; and the slope value is determined through a following formula: $k=(y_{max}-y_{min})/(F_2-F_1)$, where $y_{max}$ is a maximum value of the current data in the current data set, $y_{min}$ is a minimum value of the current data in the current data set, $F_1$ is a minimum moment data value in a moment interval, and $F_2$ is a maximum moment data value in the moment interval.

3. The method according to claim 1, wherein the step of searching for a conversion relationship corresponding to the to-be-processed current data from a pre-stored current conversion relationship table comprises steps of:

searching for a current value range to which the to-be-processed current data belongs from the pre-stored current conversion relationship table; and determining the conversion relationship corresponding to the found current value range as the conversion relationship corresponding to the to-be-processed current data.

4. The method according to claim 1, wherein the step of converting the to-be-processed current data into a corresponding target moment using the conversion relationship comprises steps of:

generating a linear expression of a conversion between the current and the moment according to the conversion relationship; and converting the to-be-processed current data into a corresponding target moment through the linear expression.

5. The method according to claim 1, wherein the step of collecting a plurality of current data generated after the load weights are placed on the ankle joint motor comprises steps of:

collecting a plurality of initial current data generated after the load weights are placed on the ankle joint motor; and filtering the initial current data to obtain the current data.

6. The method according to claim 5, wherein the step of filtering the initial current data to obtain the current data comprises:

selecting a predetermined number of initial current data from the plurality of initial current data based on a preset sampling frequency;

sorting the predetermined number of initial current data, and removing a boundary data in the sorted predetermined number of initial current data, so as to obtain a residual current data;

performing a linear regression on the residual current data; and determining an average value of the residual current data after the linear regression, and determining the average value as the current data.

7. The method according to claim 6, wherein the step of performing a linear regression on the residual current data comprises steps of:

determining whether a difference value between every two adjacent residual current data in the residual current data is greater than a preset standard deviation; and if so, removing the residual current data close to the boundary in two adjacent residual current data until the difference value between every two adjacent residual current data in the residual current data satisfies the preset standard deviation.

8. The method according to claim 7, wherein the residual current data is sorted, and wherein the step of determining whether a difference value between every two adjacent residual current data in the residual current data is greater than a preset standard deviation comprises steps of:

comparing the sorted residual current data from the minimum value to the maximum value sequentially, so as to determine whether a difference value between every two adjacent residual current data is greater than a preset standard deviation; or comparing the sorted residual current data from the maximum value to the minimum value sequentially, so as to determine whether a difference value between every two adjacent residual current data is greater than a preset standard deviation.

9. The method according to claim 1, wherein the sitting and lying adjustment angle is read by an encoder at a sitting and lying adjustment joint of the rehabilitation robot, and the ankle joint motion angle is read by the ankle joint encoder of the rehabilitation robot, wherein when a user uses the rehabilitation robot and lifts up a foot, an angle of the ankle joint motion angle is a positive value; and when the user uses the rehabilitation robot and puts down the foot, the angle of the ankle joint motion angle is a negative value.

10. A rehabilitation robot, configured for implementing a method for converting a current and a moment, applied to a controller of the rehabilitation robot, wherein the controller is electrically connected to an ankle joint motor, an ankle joint encoder and a sitting and lying adjustment joint encoder of the rehabilitation robot; the ankle joint motor of the rehabilitation robot is configured with load weights and a cantilever, the cantilever is coaxially disposed with a rotating shaft of the ankle joint motor; scale marks are disposed on the cantilever, the load weights are suspended at corresponding scale mark positions of the cantilever, and the rehabilitation robot is correspondingly configured with a force arm length and an ankle joint motion angle, as well as a sitting and lying adjustment angle corresponding to a foot pedal of the rehabilitation robot, wherein the method comprises steps of:

acquiring a to-be-processed current data;

searching for a conversion relationship corresponding to the to-be-processed current data from a pre-stored current conversion relationship table based on the to-be-processed current data, wherein the current conversion relationship table stores at least one set of corresponding relationships between current data and the conversion relationship;

converting the to-be-processed current data into a corresponding target moment using the conversion relationship, collecting a plurality of current data generated after the load weights are placed on the ankle joint motor;

acquiring the force arm length and the ankle joint motion angle of the rehabilitation robot, as well as the sitting and lying adjustment angle corresponding to the foot pedal of the rehabilitation robot, so as to obtain influencing parameter values corresponding to the moment calculation formula;

substituting the influencing parameter values and the mass data of the load weights into the moment calculation formula for calculation, so as to obtain a moment data corresponding to the current data generated by each of the load weights, wherein the moment calculation formula is: $M=F*L*\cos|(\alpha-\delta)|$;

generating a current and moment curve based on the current data and the moment data corresponding to the current data;

extracting a plurality of linear moment intervals in the current and moment curve;

calculating a slope value of each of the linear moment intervals, and saving the slope value as a conversion relationship corresponding to the linear moment intervals;

extracting current value ranges of the linear moment intervals on the current and moment curve; and associating and saving the current value ranges and the conversion relationship, so as to generate the current conversion relationship table.

11. The method according to claim 1, wherein a plurality of current data corresponding to each moment data form a current data set; and the slope value is determined through a following formula: $k=(y_{max}-y_{min})/(F_2-F_1)$, where $y_{max}$ is a maximum value of the current data in the current data set, $y_{min}$ is a minimum value of the current data in the current data set, $F_1$ is a minimum moment data value in the moment interval, and $F_2$ is a maximum moment data value in the moment interval.

12. The method according to claim 3, wherein the step of converting the to-be-processed current data into a corresponding target moment using the conversion relationship comprises steps of:

generating a linear expression of a conversion between the current and the moment according to the conversion relationship; and converting the to-be-processed current data into a corresponding target moment through the linear expression.

* * * * *